United States Patent [19]

Rasberger et al.

[11] Patent Number: 4,661,594

[45] Date of Patent: Apr. 28, 1987

[54] CERTAIN [(2,2,6,6-TETRAMETHYL-4-PIPERIDYL-)AMINO]-1,3,2-DIOXAPHOSPHORINANES USEFUL AS STABILIZERS FOR PROTECTING RESINS

[75] Inventors: Michael Rasberger, Riehen; Peter Hofmann, Basel; Hans R. Meier; Paul Dubs, both of Marly, all of Switzerland

[73] Assignee: Ciba-Geigy Corporation, Ardsley, N.Y.

[21] Appl. No.: 702,994

[22] Filed: Feb. 19, 1985

[30] Foreign Application Priority Data

Feb. 29, 1984 [CH] Switzerland ............... 964/84

[51] Int. Cl.$^4$ .................. C07F 9/65; C08K 5/51
[52] U.S. Cl. ..................... 546/22; 524/99; 524/103; 524/106; 524/107
[58] Field of Search ......................... 546/22

[56] References Cited

U.S. PATENT DOCUMENTS 3,684,765  8/1972  Matsui et al. ............... 524/99
4,191,683  4/1980  Brunetti et al. ............. 524/102

FOREIGN PATENT DOCUMENTS 2349962  4/1974  Fed. Rep. of Germany ...... 524/102
2656999  6/1977  Fed. Rep. of Germany ...... 524/103

OTHER PUBLICATIONS

H. J. Lucas et al., J. Am. Chem. Soc. 72, 5491 (1950).

Primary Examiner—Alan L. Rotman
Attorney, Agent, or Firm—Luther A. R. Hall

[57] ABSTRACT

Compounds of the formula I or II,

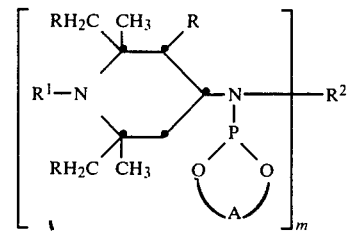

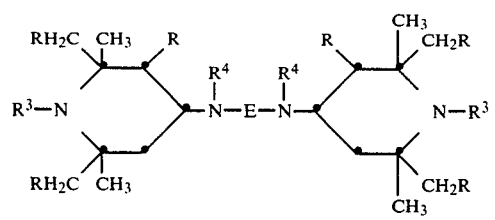

wherein m is 1 or 2, A is branched or unbranched 1,2- or 1,3-alkylene, or o-phenylene, E is a group III or IIIa, R is hydrogen or methyl, $R^1$ and $R^3$ are hydrogen, alkyl, alkenyl, aralkyl, alkanoyl, alkenoyl, benzoyl or cyanomethyl, $R^2$ is a radical of valency m and $R^4$ is a monovalent radical, are effective processing stabilizers for polymers, in particular for polyolefins, and additionally have a stabilizing action against damage by light.

5 Claims, No Drawings

CERTAIN [(2,2,6,6-TETRAMETHYL-4-PIPERIDYL)AMINO]-1,3,2-DIOXAPHOSPHORINANES USEFUL AS STABILIZERS FOR PROTECTING RESINS

The invention relates to novel polyalkylpiperidine derivatives of cyclic phosphites, their preparation and their use as stabilizers for organic polymers. The polyalkylpiperidine derivatives are P-piperidylamino derivatives of 1,3,2-dioxaphosphorinanes, 1,3,2-dioxaphospholanes, 2,4,8,10-tetraoxa-3,9-diphospha[5,5]-spiroundecane and 1,3-bis[1,3,2-dioxaphosphorinan-5-yl]-2-oxapropane.

It is known that certain cyclic phosphites, like triaryl phosphites, are good processing stabilizers for polymers. They protect the polymers during thermal processing from thermo-oxidative damage such as molecular weight degradation, crosslinking or discolouration. For these purposes, they are frequently used in combination with antioxidants of the sterically hindered phenol type, it being possible for the phosphites to have a synergistic action as costabilizers, even in small quantities. An example of a cyclic phosphite used in practice is P,P'-bis(2,4-ditert.-butylphenoxy)-2,4,8,10-tetraoxa-3,9-diphospha[5,5]spiroundecane.

Such cyclic phosphites largely lack a light stabilizing action. There has therefore been no shortage of attempts to give these compounds a light stabilizing action as well, by introducing sterically hindered amine radicals, especially 2,2,6,6-tetramethylpiperidine radicals. Thus, German Offenlegungsschrift No. 26 56 999 proposed cyclic phosphites of the general formula

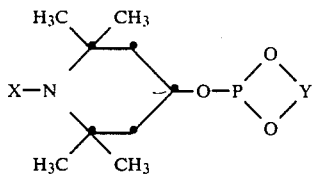

wherein X is hydrogen, oxy or a monovalent organic radical and Y is a divalent radical of a 1,2- or 1,3-diol or the radical

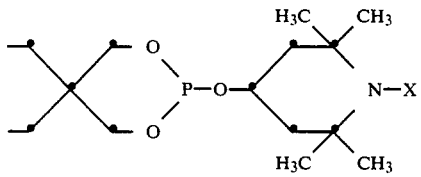

Although compounds of these types have a good light stabilizing action, they are unsatisfactory as regards storage stability, sensitivity to hydrolysis and migration behaviour, and their action as processing stabilizers is only moderate.

Surprisingly, it has been found that compounds analogous to these, in which the piperidine radical is bonded to the phosphorus not via oxygen but via nitrogen, are outstandingly effective both as light stabilizers and as processing stabilizers. They are also superior to the oxygen analogues in terms of water uptake and stability to hydrolysis. In particular, they have a good light stabilizing action even in very small concentrations.

The invention therefore relates to compounds of the formula I or II

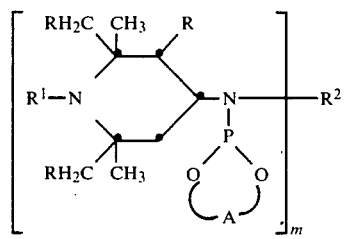

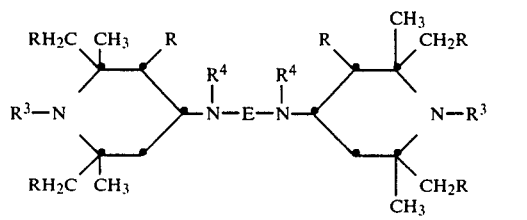

wherein
m is 1 or 2,
A is branched or unbranched 1,2- or 1,3-alkylene having 2–8 C atoms, or o-phenylene,
E is a divalent group of the formula III or IIIa

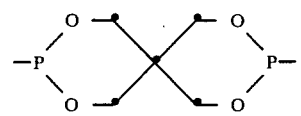

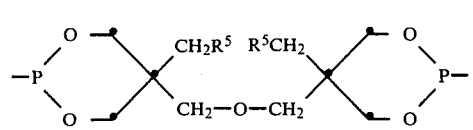

R is hydrogen or methyl,
$R^1$ is hydrogen, $C_1$–$C_{12}$-alkyl, $C_3$–$C_5$-alkenyl, $C_7$–$C_9$-aralkyl, $C_2$–$C_{12}$-alkanoyl, $C_3$–$C_6$-alkenoyl, benzoyl or cyanomethyl,
$R^2$, in the case where m=1, is $C_1$–$C_{20}$-alkyl, $C_3$–$C_{14}$-alkoxyalkyl, $C_4$–$C_{12}$-dialkylaminoalkyl, $C_5$–$C_{12}$-cycloalkyl, $C_7$–$C_9$-aralkyl, $C_6$–$C_{10}$-aryl, $C_7$–$C_{20}$-alkaryl or a group of the formula IV

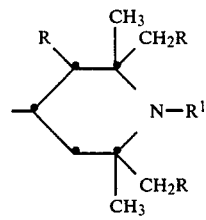

and, in the case where m=2, is $C_2$–$C_{20}$-alkylene, $C_4$–$C_{12}$-alkylene interrupted by one or more groups —O—, —N($C_1$–$C_4$-alkyl)— or

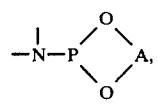

cyclohexylene, xylylene, phenylene or a group phenylene-Z-phenylene or cyclohexylene-Z-cyclohexylene, wherein Z is —O—, —CH$_2$— or —SO$_2$—, R$^3$ is hydrogen, C$_1$–C$_{12}$-alkyl, C$_3$–C$_5$-alkenyl, C$_7$–C$_9$-aralkyl, C$_2$–C$_{12}$-alkanoyl, C$_3$–C$_6$-alkenoyl, benzoyl or cyanomethyl, R$^4$ is C$_1$–C$_{20}$-alkyl, C$_3$–C$_{14}$-alkoxyalkyl, C$_4$–C$_{12}$-dialkylaminoalkyl, C$_7$–C$_9$-aralkyl, C$_6$–C$_{10}$-aryl, C$_7$–C$_{20}$-alkaryl, C$_5$–C$_{12}$-cycloalkyl or a group of the formula IV, and R$^5$ is hydrogen or methyl.

The group A is a branched or unbranched 1,2- or 1,3-alkylene group which forms a 5-membered or 6-membered ring together with the phosphorus atom and the two oxygen atoms. Unbranched groups A can be 1,2-ethylene or 1,3-propylene and branched groups A can be, for example, 1,2-propylene, 1,2-butylene, tetramethyl-1,2-ethylene, 2,2-dimethyl-1,3-propylene, 2-methyl-2-ethyl-1,3-propylene or 1,1,3-trimethyl-1,3-propylene. A is preferably a branched 1,2- or 1,3-alkylene group, especially a branched 1,3-alkylene group. Compounds of the formula I wherein A is a 2,2-dimethyl-1,3-propylene group are particularly preferred.

Alkyl R$^1$ and R$^3$ can be, for example, methyl, ethyl, propyl, butyl, isobutyl, isoamyl, hexyl, octyl, decyl or dodecyl. Alkyl R$^2$ and R$^4$ can furthermore also be, for example, tetradecyl, hexadecyl, octadecyl or eicosyl. R$^2$ and R$^4$ can also be higher alkyl mixtures such as those present in industrial fatty amines. Alkoxyalkyl R$^2$ and R$^4$ can be, for example, 2-methoxyethyl, 2-butoxyethyl, 3-ethoxypropyl, 3-methoxypropyl or 3-butoxypropyl. Dialkylaminoalkyl R$^2$ and R$^4$ can be, for example, 2-dimethylaminoethyl, 3-dimethylaminopropyl, 3-diethylaminopropyl or 3-dibutylaminopropyl.

Alkenyl R$^1$ and R$^3$ are preferably alkenylmethyl, for example allyl, methallyl, 2-butenyl or 2-methyl-2-butenyl. Allyl is preferred.

Aralkyl R$^1$, R$^2$, R$^3$ and R$^4$ can be, for example, benzyl, 2-phenylethyl, 1-phenylethyl or 3-phenylpropyl. Benzyl is preferred.

Aryl R$^2$ and R$^4$ can be phenyl or naphthyl. Alkaryl R$^2$ and R$^4$ are especially alkylphenyl and can be, for example, tolyl, xylyl, ethylphenyl, tert.-butylphenyl, nonylphenyl, dodecylphenyl, methylnaphthyl or nonylnaphthyl. Cycloalkyl R$^2$ and R$^4$ can be, for example, cyclopentyl, cyclohexyl, cycloheptyl or cyclooctyl. Cyclohexyl is preferred.

Alkanoyl or alkenoyl R$^1$ and R$^3$ can be, for example, acetyl, propionyl, butyroyl, hexanoyl, octanoyl, dodecanoyl, acryloyl, methacryloyl or crotonyl. Acetyl is preferred.

In the case where m=2, R$^2$ is a divalent radical and can be, for example, 1,2-ethylene, tri-, tetra-, hexa-, octa-, deca- or dodeca-methylene, 2,2,4-trimethylhexamethylene, 2-methylpentamethylene, 4-oxaheptamethylene, 4,7-dioxadecamethylene, 4-isopropylazaheptamethylene, 3,6-di(methylaza)octamethylene, 1,4-cyclohexylene, m- or p-xylylene, m- or p-phenylene, diphenyl ether 4,4'-diyl, diphenylmethane-4,4'-diyl, diphenyl sulfone 4,4'-diyl, dicyclohexylmethane-4,4'-diyl or dicyclohexyl sulfone 4,4'-diyl. Divalent radical R$^2$ is preferably a C$_2$–C$_{18}$-alkylene group, especially a C$_2$–C$_{10}$-alkylene group.

Preferred compounds of the formula I or II are those wherein A is branched 1,2- or 1,3-alkylene, E is a group of the formula III, R is hydrogen, R$^1$ is hydrogen, methyl, allyl, benzyl or acetyl, R$^2$ is C$_1$–C$_{18}$-alkyl, a group of the formula IV or C$_2$–C$_{10}$-alkylene, R$^3$ is hydrogen, methyl, allyl, benzyl or acetyl and R$^4$ is C$_1$–C$_{18}$-alkyl or a group of the formula IV.

Particularly preferred compounds of the formula I or II are those wherein A is branched 1,3-propylene, E is a group of the formula III, R is hydrogen, R$^1$ and R$^3$ are hydrogen or methyl, R$^2$ is C$_1$–C$_{12}$-alkyl, a group of the formula IV or C$_2$–C$_8$-alkylene and R$^4$ is C$_1$–C$_{12}$-alkyl or a group of the formula IV, especially those wherein A is a group of the formula —CH(R$^6$)—C(CH$_3$)$_2$—CH$_2$—, wherein R$^6$ H is hydrogen or C$_1$–C$_4$-alkyl.

Examples of specific compounds of the formula I are: 5,5-dimethyl-2-[N-ethyl(2,2,6,6-tetramethyl-4-piperidyl)amino]1,3,2-dioxaphosphorinane, 2-[N-butyl(1,2,2,6,6-pentamethyl-4-piperidyl)amino]-5,5-dimethyl-1,3,2-dioxaphosphorinane, 5,5-dimethyl-2-[N-2-ethylhexyl(2,2,6,6-tetramethyl-4-piperidyl)amino]-1,3,2-dioxaphosphorinane, 2-[N-butyl(1-allyl-2,2,6,6-tetramethyl-4-piperidyl)amino]-5-ethyl-5-methyl-1,3,2-dioxaphosphorinane, 2-[N-benzyl(2,2,6,6-tetramethyl-4-piperidyl)amino]-5,5-dimethyl-4-propyl-1,3,2-dioxaphosphorinane, 2-[N-(1-acetyl-2,2,6,6-tetramethyl-4-piperidyl)anilino]-5,5-dimethyl-4-isopropyl-1,3,2-dioxaphosphorinane, 2-[N,N-bis(2,2,6,6-tetramethyl-4-piperidyl)amino]-4,4,6-trimethyl-1,3,2-dioxaphosphorinane, 2-[N-butyl(2,2,6,6-tetramethyl-4-piperidyl)amino]-5-ethyl-4-propyl-1,3,2-dioxaphosphorinane, 2-[N-(1-acrylyl-2,2,6,6-tetramethyl-4-piperidyl)cyclohexylamino]-4-methyl-1,3,2-dioxaphosphorinane, 2-[N-(2-methoxyethyl)(2,2,6,6-tetramethyl-4-piperidyl)amino]-1,3,2-dioxaphosphorinane, 2-[N-butyl(2,6-diethyl-2,3,6-trimethyl-4-phosphorinane, piperidyl)amino]-5,5-dimethyl-1,3,2-dioxaphosphorinane, 2-[N-benzyl(2,6-diethyl-1,2,3,6-trimethyl-4-piperidyl)amino]-4,4,6-trimethyl-1,3,2-dioxaphosphorinane, 2-[N,N-bis(2,6-diethyl-2,3,6-trimethyl-4-piperidyl)amino]-5,5-dimethyl-1,3,2-dioxaphosphorinane, 2-[N-butyl(2,2,6,6-tetramethyl-4-piperidyl)amino]-1,3,2-dioxaphospholane, 2-[N-dodecyl(1,2,6,6-pentamethyl-4-piperidyl)amino]-4-methyl-1,3,2-dioxapholane, 2-[N-(1-benzyl-2,2,6,6-tetramethyl-4-piperidyl)octylamino]-4-ethyl-1,3,2-dioxaphospholane, 2-[N-benzyl(2,2,6,6-tetramethyl-4-piperidyl)amino]-4,5-dimethyl-1,3,2-dioxaphospholane, 2-[N-(1-acetyl-2,2,6,6-tetramethyl-4-piperidyl)anilino]-4,4,5,5-tetramethyl-1,3,2-dioxaphospholane, 4,5-diethyl-4,5-dimethyl-2-[N-(2-dimethylaminoethyl)-2,2,6,6-tetramethyl-4-piperidyl)amino]-1,3,2-dioxaphospholane, 2-[N-(2,6-diethyl-2,3,6-trimethyl-4-piperidyl)dodecylamino]-4,4,5,5-tetramethyl-1,3,2-dioxaphospholane, N,N'-bis(5,5-dimethyl-1,3,2-dioxaphosphorinan-2-yl)-N,N'-bis(2,2,6,6-tetramethyl-4-piperidyl)ethylenediamine, N,N'-bis(1,2,2,6,6-pentamethyl-4-piperidyl)-N,N'-bis(4,4,6-trimethyl-1,3,2-dioxaphosphorinan-2-yl)trimethylenediamine, N,N'-bis(1-allyl-2,2,6,6-tetramethyl-4-piperidyl)-N,N'-bis(5-ethyl-5-methyl-1,3,2-dioxaphosphorinan-2-yl)hexamethylenediamine, N,N'-bis(1-benzyl-2,2,6,6-tetramethyl-4-piperidyl)-N,N'-bis(5-ethyl-4-propyl-1,3,2-dioxaphosphorinan-2-yl)-2,2'-diaminodiethyl ether, N,N''-bis(2,2,6,6-tetramethyl-4-piperidyl)-N,N',N''-tris(5,5-dimethyl-1,3,2-dioxaphosphorinan-2-yl)diethylenetriamine, 1,12-bis(2,2,6,6-tetramethyl-4-piperidyl)-1,5,8,12-tetrakis(4,4,6-trimethyl-1,3,2-dioxaphosphorinan-2-yl)-1,5,8,12-tetraazadodecane, N,N''-bis(4-methyl-1,3,2-dioxaphosphorinan-2-yl)-N,N'''-bis(2,2,6,6-tetramethyl-4-piperidyl)-N'-methyldiethylenetriamine, N,N'-bis(4,4,5,5-tetramethyl-1,3,2-dioxaphospholan-2-yl)-N,N'-bis(2,2,6,6-tetramethyl-4-piperidyl)octamethylenediamine, N,N'-bis(2,6-diethyl- 2,3,6-trimethyl-4-piperidyl)-N,N'-bis(4,5-dimethyl-1,3,2-dioxaphospholan-2-yl)hexamethylenediamine and N,N'''-bis(2,6-diethyl-2,3,6-trimethyl-4-piperidyl)-N,N',N''-tris(5,5-dimethyl-1,3,2-dioxaphosphorinan-2-yl)diethylenetriamine.

Examples of specific compounds of the formula II are: 3,9-bis[N-propyl(2,2,6,6-tetramethyl-4-piperidyl)amino]-2,4,8,10-tetraoxa-3,9-diphosphaspiro[5,5]undecane, 3,9-bis[N-(1-allyl-2,2,6,6-tetramethyl-4-piperidyl)-N-2-ethylhexylamino]-2,4,8,10-tetraoxa-3,9-diphosphaspiro[5,5]undecane, 3,9-bis[N-(2-dimethylaminoethyl)-1,2,2,6,6-pentamethyl-4-piperidylamino]-2,4,8,10-tetraoxa-3,9-diphosphaspiro[5,5]undecane, 3,9-bis[N-(1-acetyl-2,2,6,6-tetramethyl-4-piperidyl)dodecylamino]-2,4,8,10-tetraoxa-3,9-diphosphaspiro[5,5]undecane, 3,9-bis[N-(2,6-diethyl-2,3,6-trimethyl-4-piperidyl)dodecylamino]-2,4,8,10-tetraoxa-3,9-diphosphaspiro[5,5]undecane, 1,3-bis[2-(N-bis(1,2,2,6,6-pentamethyl-4-piperidyl)amino)-5-ethyl-1,3,2-dioxaphosphorinan-5-yl]-2-oxapropane, 1,3-bis[2-(N-(2-methylpropyl)-N-(2,2,6,6-tetramethyl-4-piperidyl)amino)-5-methyl-1,3,2-dioxaphosphorinan-5-yl]-2-oxapropane and 1,3-bis[2-(N-(2-ethylhexyl)-N-(2,2,6,6-tetramethyl-4-piperidyl)amino)-5-ethyl-1,3,2-dioxaphosphorinan-5-yl]-2-oxapropane.

The compounds of the formula I can be prepared by a general method in which a secondary piperidylamine of the formula V is reacted with a phosphochloridite of the formula VI:

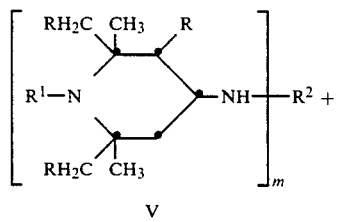

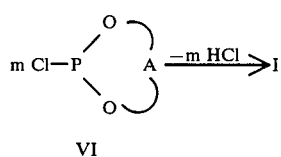

The compounds of the formula II can be prepared analogously by reacting a bisphosphochloridite Cl-E-Cl with 2 mol of an amine of the formula VII:

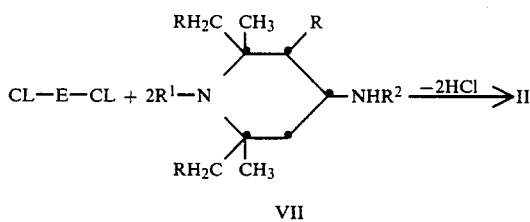

The phosphochloridites of the formula VI or Cl-E-Cl and the amines V or VII are known compounds. The phosphochloridites can be prepared from the corresponding diols and PCl$_3$ in the manner described, for example, in J. Amer. Chem. Soc. 72 (1950) 5491-7. The amines are preferably prepared from the corresponding 4-ketopiperidines by reductive amination in the manner described, for example, in German Offenlegungsschriften Nos. 2,040,975, 2,349,962 and 2,621,870.

The reaction is performed by adding the compound VI or Cl-E-Cl, or a solution thereof in an inert solvent, to a solution of the amine V or VII. The reaction can be brought to completion by heating. Examples of suitable solvents are benzene, toluene, xylene, dioxane, dimethoxyethane, methylene chloride, ethyl acetate, acetonitrile or dimethylformamide.

The reaction can also be carried out without a solvent if the components and the reaction product melt at sufficiently low temperatures. Reaction temperatures of 100°-150° C. are preferably used in this case.

To neutralize the hydrogen chloride, a base is added to the reaction mixture in at least an equivalent quantity. The base can be, for example, an alkali metal hydroxide, an alkaline earth metal hydroxide or oxide, ammonia or a tertiary amine. It is also possible to use the amine as a solvent, suitable examples for this purpose being triethylamine or tributylamine.

The salt formed by neutralization can be removed from the reaction mixture by, for example, filtration or extraction with water. The solvent is then distilled off to give the crude product of the formula I or II as a residue, which can be purified by conventional purification methods, for example recrystallization of column chromatography.

In place of the phosphochloridites VI or Cl-E-Cl, it is also possible to use the corresponding phosphoamidites of the formula VIII

or (Alk)$_2$N-E-N(Alk)$_2$, wherein Alk is a lower alkyl radical. This method requires catalytic quantities of a base and is preferably carried out without a solvent. Strong bases, for example LiH, NaH and LiNH$_2$, are used as the catalyst. The reaction is preferably carried out at 100°-180° C., the dialkylamine formed, (Alk)$_2$NH, being distilled off simultaneously.

In place of the phosphochloridites, it is also possible to use the corresponding alkoxy or aryloxy compounds. In this case, the reaction is carried out in the same way as with the phosphoamidites.

The compounds of the formulae I and II can be used according to the present invention as stabilizers for protecting organic polymers against damage by heat, oxygen and light. Examples of such polymers are:

1. Polymers of monoolefins and diolefins, for example polyethylene (which may or may not be crosslinked), polypropylene, polyisobutylene, polybut-1-ene, polymethylpent-1-ene, polyisoprene or polybutadiene, as well as polymers of cycloolefins, for example of cyclopentene or norbornene.

2. Mixtures of the polymers mentioned under (1), for example mixtures of polypropylene with polyisobutylene.

3. Copolymers of monoolefins and diolefins with one another or with other vinyl monomers, for example ethylene/propylene copolymers, propylene/but-1-ene copolymers, propylene/isocopolymers, butylene copolymers, ethylene/but-1-ene copolymers, propylene/butadiene copolymers, isobutylene/isoprene copolymers, ethylene/alkyl acrylate copolymers, ethylene/alkyl methacrylate copolymers, ethylene/vinyl acetate copolymers or ethylene/acrylic acid copolymers and their salts (ionomers), as well as terpolymers of ethylene with propylene and a diene such as hexadiene, dicyclopentadiene or ethylidenenorbornene.

4. Polystyrene and poly(p-methylstyrene).

5. Copolymers of styrene or =<-methylstyrene with dienes or acrylic derivatives, for example styrene/butadiene, styrene/acrylonitrile, styrene/alkyl methacrylate, styrene/maleic anhydride and styrene/acrylonitrile/methyl acrylate; high impact strength mixtures of styrene copolymers and another polymer such as a polyacrylate, a diene polymer or an ethylene/propylene/diene terpolymer; and block copolymers of styrene, for example styrene/butadiene/styrene, styrene/isoprene/styrene, styrene/ethylene-butylene/styrene or styrene/ethylene-propylene/styrene.

6. Graft copolymers of styrene, for example styrene grafted onto polybutadiene, styrene and acrylonitrile grafted onto polybutadiene, styrene and maleic anhydride grafted onto polybutadiene, styrene and alkyl acrylates or alkyl methacrylates grafted onto polybutadiene, styrene and acrylonitrile grafted onto ethylene/propylene/diene terpolymers, styrene and acrylonitrile grafted onto polyalkyl acrylates or polyalkyl methacrylates, and styrene and acrylonitrile grafted onto acrylate/butadiene copolymers, as well as mixtures thereof with the copolymers given under (5), for example those known as so-called ABS, MBS, ASA or AES polymers.

7. Halogen-containing polymers, for example polychloroprene, chlorinated rubber, chlorinated or chlorosulfonated polyethylene, epichlorohydrin homopolymers and copolymers, especially polymers of halogen-containing vinyl compounds, for example polyvinyl chloride, polyvinylidene chloride, polyvinyl fluoride and polyvinylidene fluoride, as well as covinyl polymers thereof, such as vinyl chloride/vinylidene chloride, vinyl chloride/vinyl acetate or vinylidene chloride/vinyl acetate.

8. Polymers derived from α,β-unsaturated acids and derivatives thereof, such as polyacrylates and polymethacrylates, polyacrylamides and polyacrylonitriles.

9. Copolymers of the monomers given under (8) with one another or with other unsaturated monomers, for example acrylonitrile/butadiene copolymers, acrylonitrile/alkyl acrylate copolymers, acrylonitrile/alkoxyalkyl acrylate copolymers, acrylonitrile/vinyl halide copolymers or acrylonitrile/alkyl methacrylate/butadiene terpolymers.

10. Polymers derived from unsaturated alcohols and amines or their acyl derivatives or acetals, such as polyvinyl alcohol, polyvinyl acetate, stearate, benzoate or maleate, polyvinylbutyral, polyallyl phthalate and polyallylmelamine.

11. Homopolymers and copolymers of cyclic ethers, such as polyalkylene glycols, polyethylene oxide, polypropylene oxide or copolymers thereof with bisglycidyl ethers.

12. Polyacetals such as polyoxymethylene, as well as polyoxymethylenes containing comonomers such as ethylene oxide.

13. Polyphenyl oxides and sulfides and mixtures thereof with styrene polymers.

14. Polyurethanes derived on the one hand from polyethers, polyesters and polybutadienes with terminal hydroxyl groups and on the other hand from aliphatic or aromatic polyisocyanates, as well as precursors thereof.

15. Polyamides and copolyamides derived from diamines and dicarboxylic acids and/or from aminocarboxylic acids or the corresponding lactams, such as polyamide 4, polyamide 6, polyamide 6,6, polyamide 6,10, polyamide 11, polyamide 12, poly-2,4,4-trimethylhexamethyleneterephthalamide and poly-m-phenyleneisophthalamide, as well as block copolymers thereof with polyethers, for example with polyethylene glycol, polypropylene glycol or polytetramethylene glycol.

16. Polyureas, polyimides, polyamide-imides and polybenzimidazoles.

17. Polyesters derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates, as well as block polyether-esters derived from polyethers with terminal hydroxyl groups.

18. Polycarbonates and polyester-carbonates.

19. Polysulfones, polyether-sulfones and polyetherketones.

20. Crosslinked polymers derived on the one hand from aldehydes and on the other hand from phenols, urea or melamine, such as phenol/formaldehyde, urea/formaldehyde and melamine/formaldehyde resins.

21. Drying and non-drying alkyd resins.

22. Unsaturated polyester resins derived from copolyesters of saturated and unsaturated dicarboxylic acids with polyhydric alcohols, and from vinyl compounds as crosslinking agents, as well as slow-burning halogen-containing modifications thereof.

23. Crosslinkable acrylic resins derived from substituted acrylic acid esters, for example from epoxyacrylates, urethane-acrylates or polyester-acrylates.

24. Alkyd resins, polyester resins and acrylate resins crosslinked with melamine resins, urea resins, polyisocyanates or epoxy resins.

25. Crosslinked epoxy resins derived from polyepoxides, for example from bisglycidyl ethers or from cycloaliphatic diepoxides.

26. Natural polymers such as cellulose, natural rubber and gelatine, as well as polymer-homologously, chemically modified derivatives thereof, such as cellulose acetates, propionates and butyrates, or cellulose ethers such as methyl cellulose.

27. Mixtures (polyblends) of the abovementioned polymers, for example PP/EPDM, polyamide 6/EPDM or ABS, PVC/EVA, PVC/ABS, PVC/MBS, PC/ABS and PBTP/ABS.

The stabilization of polyolefins and styrene polymers, such as those listed in sections 1-6, is of particular importance.

The compounds of the formulae I and II are added to the polymer in a concentration of 0.001 to 2% by weight based on the polymer to be stabilized. 0.025 to 0.2% by weight is preferably added. Incorporation into the polymer to be stabilized can be effected by mixing in the stabilizers and, if appropriate, other additives by the methods conventionally used in the art, before or during the shaping of the polymer. The compounds of the formulae I and II can also be added to the polymers as a master batch containing these compounds in a concentration of, for example, 2.5 to 25% by weight.

The invention therefore relates also to the organic polymers stabilized by the addition of 0.001 to 2% by weight of a compound of the formula I or II, it also being possible, if appropriate, for the said polymers to contain other additives conventionally used in polymer technology.

The following are examples of other additives together with which the stabilizers according to the invention can be used:

1. Antioxidants 1.1. Alkylated monophenols 2,6-Ditert.-butyl-4-methylphenol, 2-tert.-butyl-4,6-dimethylphenol, 2,6-ditert.-butyl-4-ethylphenol, 2,6-ditert.-butyl-4-n-butylphenol, 2,6-ditert.-butyl-4-i-butylphenol, 2,6-dicyclopentyl-4-methylphenol, 2-( -methylcyclohexyl)-4,6-dimethylphenol, 2,6-dioctadecyl-4-methylphenol, 2,4,6-tricyclohexylphenol and 2,6-ditert.-butyl-4-methoxymethylphenol.

1.2. Alkylated hydroquinones 2,6-Ditert.-butyl-4-methoxyphenol, 2,5-ditert.-butylhydroquinone, 2,5-ditert.-amylhydroquinone and 2,6-diphenyl-4-octadecyloxyphenol.

1.3. Hydroxylated thiodiphenyl ethers 2,2'-Thiobis(6-tert.-butyl-4-methylphenol), 2,2'-thiobis(4-octylphenol), 4,4'-thiobis(6-tert.-butyl-3-methylphenol) and 4,4'-thiobis(6-tert.-butyl-2-methylphenol).

1.4. Alkylidenebisphenols 2,2'-Methylenebis(6-tert.-butyl-4-methylphenol), 2,2'-methylenebis(6-tert.-butyl-4-ethylphenol), 2,2'-methylenebis[4-methyl-6-( -methylcyclohexyl)phenol], 2,2'-methylenebis(4-methyl-6-cyclohexylphenol), 2,2'-methylenebis(6-nonyl-4-methylphenol), 2,2'-methylenebis(4,6-ditert.-butylphenol), 2,2'-ethylidenebis(4,6-ditert.-butylphenol), 2,2'-ethylidenebis(6-tert.-butyl-4-isobutylphenol), 2,2'-methylenebis[6-(methylbenzyl)-4-nonylphenol], 2,2'-methylenebis[6-(, -dimethylbenzyl)-4-nonylphenol], 4,4'-methylenebis(2,6-ditert.-butylphenol), 4,4'-methylenebis(6-tert.-butyl-2-methylphenol), 1,1-bis(5-tert.-butyl-4-hydroxy-2-methylphenyl)butane, 2,6-di(3-tert.-butyl-5-methyl-2-hydroxybenzyl)-4-methylphenol, 1,1,3-tris(5-tert.-butyl-4-hydroxy-2-methylphenyl)butane, 1,1-bis(5-tert.-butyl-4-hydroxy-2-methylphenyl)-3-n-dodecylmercaptobutane, ethylene glycol bis[3,3-bis(3'-tert.-butyl-4'-hydroxyphenyl)butyrate], di(3-tert.-butyl-4-hydroxy-5-methylphenyl)dicyclopentadiene and di[2-(3'-tert.-butyl-2'-hydroxy-5'-methylbenzyl)-6-tert.-butyl-4-methylphenyl]terephthalate.

1.5. Benzyl compounds 1,3,5-Tri(3,5-ditert.-butyl-4-hydroxybenzyl)-2,4,6-trimethylbenzene, di(3,5-ditert.-butyl-4-hydroxybenzyl) sulfide, isooctyl 3,5-ditert.-butyl-4-hydroxybenzylmercaptoacetate, bis(4-tert.-butyl-3-hydroxy-2,6-dimethylbenzyl)dithiol terephthalate, 1,3,5-tris(3,5-ditert.-butyl-4-hydroxybenzyl) isocyanurate, 1,3,5-tris(4-tert.-butyl-3-hydroxy-2,6-dimethylbenzyl) isocyanurate, dioctadecyl 3,5-ditert.-butyl-4-hydroxybenzylphosphonate and the calcium salt of monoethyl 3,5-ditert.-butyl-4-hydroxybenzylphosphonate.

1.6. Acylaminophenols

4-Hydroxylauric acid anilide, 4-hydroxystearic acid anilide, 2,4-bisoctylmercapto-6-(3,5-ditert.-butyl-4-hydroxyanilino)-s-triazine and octyl N-(3,5-ditert.-butyl-4-hydroxyphenyl)carbamate.

1.7. Esters of -(3,5-ditert.-butyl-4-hydroxyphenyl)-propionic acid with monohydric or polyhydric alcohols, for example with methanol, octadecanol, 1,6-hexanediol, neopentylglycol, thiodiethylene glycol, diethylene glycol, triethylene glycol, pentaerythritol, trishydroxyethyl isocyanurate or dihydroxyethyloxalic acid diamide.

1.8. Esters of -(5-tert.-butyl-4-hydroxy-3-methylphenyl)propionic acid with monohydric or polyhydric alcohols, for example with methanol, octadecanol, 1,6-hexanediol, neopentylglycol, thiodiethylene glycol, diethylene glycol, triethylene glycol, pentaerythritol, trishydroxyethyl isocyanurate or dihydroxyethyloxalic acid diamide.

1.9. Amides of -(3,5-ditert.-butyl-4-hydroxyphenyl)-propionic acid, for example N,N'-di(3,5-ditert.-butyl-4-hydroxyphenylpropionyl)hexamethylenediamine, N,N'-di(3,5-ditert.-butyl-4-hydroxyphenylpropionyl)-trimethylenediamine and N,N'-di(3,5-ditert.-butyl-4-hydroxyphenylpropionyl)hydrazine.

2. UV absorbers and light stabilizers 2.1. 2-(2'-Hydroxyphenyl)benztriazoles, for example the 5'-methyl, 3',5'-ditert.-butyl, 5'-tert.-butyl, 5'-(1,1,3,3,-tetramethylbutyl), 5-chloro-3',5'-ditert.-butyl, 5-chloro-3'-tert.-butyl-5'-methyl, 3'-sec.-butyl-5'-tert.-butyl, 4'-octoxy, 3',5'-ditert.-amyl or 3',5'-bis( , -dimethylbenzyl) derivative.

2.2. 2-Hydroxybenzophenones, for example the 4-hydroxy, 4-methoxy, 4-octoxy, 4-decyloxy, 4-dodecyloxy, 4-benzyloxy, 4,2',4'-trihydroxy or 2'-hydroxy-4,4'-dimethoxy derivative.

2.3. Esters of substituted or unsubstituted benzoic acids, for example 4-tert.-butylphenyl salicylate, phenyl salicylate, octylphenyl salicylate, dibenzoylresorcinol, bis(4-tert.-butylbenzoyl)resorcinol, benzoylresorcinol, 2,4-ditert-butylphenyl 3,5-ditert.-butyl-4-hydroxybenzoate and hexadecyl 3,5-ditert.-butyl-4-hydroxybenzoate.

2.4. Acrylates, for example ethyl or isooctyl -cyano-, diphenylacrylate, methyl-carbomethoxycinnamate, methyl or butyl -cyano- -methyl-p-methoxycinnamate, methyl-carbomethoxy-p-methoxycinnamate and N-(-carbomethoxy- -cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, if appropriate with additional ligands such as n-butylamine, triethanolamine or N-cyclohexyldiethanolamine, nickel dibutyldithiocarbamate, nickel salts of monoalkyl 4-hydroxy-3,5-ditert.-butylbenzylphosphonates, such as those of the methyl or ethyl ester, nickel complexes of ketoximes, such as those of 2-hydroxy-4-methylphenylundecylketonoxime, and nickel complexes of 1-phenyl-4-lauroyl-5-hydroxypyrazole, if appropriate with additional ligands.

2.6. Sterically hindered amines, for example bis(2,2,6,6-tetramehylpiperidyl) sebacate, bis(1,2,2,6,6-pentamethylpiperidyl) sebacate, bis(1,2,2,6,6-pentamethylpiperidyl) n-butyl-3,5-ditert.-butyl-4-hydroxybenzylmalonate, the condensation product of 1-hydroxyethyl-2,2,6,6-tetramethyl-4-hydroxypiperidine and succinic acid, the condensation product of N,N'-(2,2,6,6-tetramethyl-4-piperidyl)hexamethylenediamine and 4-tert.-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetracarboxylic acid and 1,1'-(1,2-ethanediyl)bis(3,3,5,5-tetramethylpiperazinone).

2.7. Oxalic acid diamides, for example 4,4'-dioctyloxyoxalic acid anilide, 2,2'-dioctyloxy-5,5'-ditert.-butyloxalic acid anilide, 2,2'-didodecyloxy-5,5'-ditert.-butyloxalic acid anilide, 2-ethoxy-2'-ethyloxalic acid anilide, N,N'-bis(3-dimethylaminopropyl)oxalamide, 2-ethoxy-5-tert.-butyl-2'-ethyloxalic acid anilide and a mixture thereof with 2'-ethyl-5,4'-ditert.-butyloxalic acid anilide, and 2-ethoxymixtures of oxalic acid anilides disubstituted by orthomethoxy and para-methoxy or by o-ethoxy and p-ethoxy.

3. Metal deactivators, for example N,N'-diphenyloxalic acid diamide, N-salicylal-N'-salicyloylhydrazine, N,N'-bissalicyloylhydrazine, N,N'-bis(3,5-ditert.-butyl-4-hydroxyphenylpropionyl)hydrazine, 3-salicyloylamino-1,2,4-triazole and bisbenzylideneoxalic acid dihydrazide.

4. Phosphites and phosphonites, for example triphenyl phosphite, diphenyl alkyl phosphites, phenyl dialkyl phosphites, tri(nonylphenyl) phosphite, trilauryl phosphite, trioctadecyl phosphite, distearyl pentaerythrityl diphosphite, tris(2,4-ditert.-butylphenyl) phosphite, diisodecyl pentaerythrityl diphosphite, di(2,4-ditert.-butylphenyl) pentaerythrityl diphosphite, tristearyl sorbityl triphosphite and tetrakis(2,4-ditert.-butylphenyl) 4,4'-biphenylene diphosphonite.

5. Compounds which destroy peroxide, for example esters of -thiodipropionic acid, such as the lauryl, stearyl, myristyl or tridecyl esters, mercaptobenzimidazole, the zinc salt of 2-mercaptobenzimidazole, zinc dibutyldithiocarbamate, dioctadecyl disulfide and pentaerythritol tetrakis( -dodecylmercapto)propionate.

6. Polyamide stabilizers, for example copper salts in combination with iodides and/or phosphorus compounds, and salts of divalent manganese.

7. Basic costabilizers, for example melamine, polyvinylpyrrolidone, dicyanodiamide, triallyl cyanurate, urea derivatives, hydrazine derivatives, amines, polyamides, polyurethanes, alkali metal and alkaline earth metal salts of higher fatty acids, for example Ca stearate, Zn stearate, Mg stearate, Na ricinoleate or K palmitate, antimony pyrocatechuate or tin pyrocatechuate.

8. Nucleating agents, for example 4-tert.-butylbenzoic acid, adipic acid and diphenylacetic acid.

9. Fillers and reinforcing agents, for example calcium carbonate, silicates, glass fibres, asbestos, talcum, kaolin, mica, barium sulfate, metal oxides and hydroxides, carbon black and graphite.

10. Other additives, for example plasticizers, lubricants, emulsifiers, pigments, fluorescent brighteners, flame retardants, antistatic agents and propellants.

When stabilizers of these types are also used, synergistic effects can occur. The concomitant use of antioxidants is of particular importance in the case of polyolefins and styrene polymers.

The polymers stabilized in this way can be used in a variety of forms, for example as films, fibres, tapes, profiles or elastic mouldings.

The examples which follow illustrate the preparation and use of the compounds according to the invention in greater detail, without the invention being restricted to the examples. Parts and percentages are by weight. The temperatures listed are given in °C.

EXAMPLE 1

18.4 g of 2-chloro-5,5-dimethyl-1,3,2-dioxaphosphorinane are added dropwise, at room temperature, with stirring, to a solution of 19.7 g (0.1 mol) of 4-butylamino1,2,2,6,6-pentamethylpiperidine in 100 ml of triethylamine. After heating at the reflux temperature for 15 hours, the mixture is diluted with toluene and the precipitated hydrochloride is filtered off. Evaporation of the filtrate gives 2-[N-butyl(1,2,2,6,6-pentamethyl-4-piperidyl)amino]-5,5-dimethyl-1,3,2-dioxaphosphorinane as an oil which boils at 120° under 40 Pa (Compound No. 1).

By using 4-butylamino-2,2,6,6-tetramethylpiperidine in a procedure analogous to that followed for Compound 1, 2-[N-butyl(2,2,6,6-tetramethyl-4-piperidyl)amino]-5,5-dimethyl-1,3,2-dioxaphosphorinane is obtained as an oil which boils at 100° under 0.04 Torr (Compound No. 2). Analysis (344.48): P calc. 8.99%, found 9.16%.

By using 21.1 g of N,N'-bis(1,2,2,6,6-pentamethyl-4-piperidyl)hexamethylenediamine in an analogous procedure, N,N'-bis(5,5-dimethyl-1,3,2-dioxaphosphorinan-2-yl)-N,N'-bis(1,2,2,6,6-pentamethyl-4-piperidyl)hexamethylenediamine is obtained, which melts at 103° after recrystallization from acetonitrile (Compound No. 3).

If N,N'-bis(2,2,6,6-tetramethyl-4-piperidyl)trimethylenediamine is used as the amine in an analogous procedure, N,N'-bis(5,5-dimethyl-1,3,2-dioxaphosphorinan-2-yl)-N,N'-bis(2,2,6,6-tetramethyl-4-piperidyl)trimethylenediamine is obtained, which melts at 102° (Compound No. 4).

By using N,N'-bis(2,2,6,6-tetramethyl-4-piperidyl)-hexamethylenediamine in an analogous procedure, N,N'-bis(5,5-dimethyl-1,3,2-dioxaphosphorinan-2-yl)-N,N'-bis(2,2,6,6-tetramethyl-4-piperidyl)hexamethylenediamine is obtained, which melts at 103° (Compound No. 5).

By using bis(2,2,6,6-tetramethyl-4-piperidyl)amine in an analogous procedure, 5,5-dimethyl-1,3,2-dioxaphosphorinan-2-ylbis(2,2,6,6-tetramethyl-4-piperidyl)amine is obtained, which melts at 156° (Compound No. 6).

The same compound is also obtained by reacting 16.8 g of 2-chloro-5,5-dimethyl-1,3,2-dioxaphosphorinane with 29.6 g of bis(2,2,6,6-tetramethyl-4-piperidyl)amine for 3 hours, without a solvent, at 150°. After cooling, the reaction mixture is taken up in toluene and extracted with aqueous ammonia and the toluene solution is evaporated.

The same compound is also obtained by reacting equimolar quantities of 2-chloro-5,5-dimethyl-1,3,2-dioxaphosphorinane and bis(2,2,6,6-tetramethyl-4-piperidyl)amine in toluene for 15 hours, under reflux, and then cleaving the salt obtained with 10% aqueous potassium hydroxide.

EXAMPLE 1a

If 2-chloro-5,5-dimethyl-4-isopropyl-1,3,2-dioxaphosphorinane is reacted with N,N'-bis(2,2,6,6-tetramethyl-4-piperidyl)hexamethylenediamine in a procedure analogous to Example 1, N,N'-bis(5,5-dimethyl-4-isopropyl-1,3,2-dioxaphosphorinan-2-yl)-N,N'-bis(2,2,6,6-tetramethyl-4-piperidyl)hexamethylenediamine is obtained, which melts at 95°–97° (Compound No. 7).

Analysis (741.00): P calc. 8.36%, found 8.32%.

In an analogous procedure, 2-chloro-5,5-dimethyl-4-isopropyl-1,3,2-dioxaphosphorinane and 4-amino-2,2,6,6-tetramethylpiperidine give 5,5-dimethyl-4-isopropyl-1,3,2-dioxaphosphorinan-2-ylbis(2,2,6,6-tetramethyl-4-piperidyl)amine, which melts at 139°–141° (Compound No. 8).

Analysis (469.67): P calc. 6.59%, found 6.59%.

EXAMPLE 2

A solution of 26.5 g of 3,9-dichloro-2,4,8,10-tetraoxa-3,9-diphosphaspiro[5,5]undecane in 60 ml of xylene is slowly added dropwise to a solution of 59.1 g of bis(2,2,6,6-tetramethyl-4-piperidyl)amine in 120 ml of triethylamine. The mixture is then heated under reflux for 20 hours and diluted with xylene, the hydrochloride is filtered off and the xylene solution is evaporated. This gives 3,9-bis[bis(2,2,6,6-tetramethyl-4-piperidyl)amino]-2,4,8,10-tetraoxa-3,9-diphosphaspiro[5,5]undecane as a residue, which melts at 265° after purification by column chromatography (Compound No. 9).

In an analogous procedure, the compounds listed in Table 1 are prepared from 3,9-dichloro-2,4,8,10-tetraoxa-3,9-diphosphaspiro[5,5]undecane and the corresponding aminopiperidines.

TABLE 1

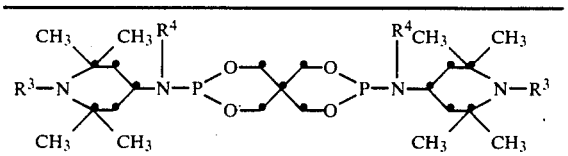

| Compound No. | $R^3$ | $R^4$ | Properties |
|---|---|---|---|
| 10 | H | cyclohexyl | melting point 184° |
| 11 | H | n-dodecyl | oil, analysis: P calc. 7.37%, found 7.27% |
| 12 | H | n-butyl | melting point 146° |
| 13 | H | isobutyl (2-methylpropyl) | melting point 147° |
| 14 | H | n-octyl | viscous resin, analysis: P calc. 8.49%, found 8.50% |
| 15 | H | 2-ethylhexyl | oil, mass spectrum: M+ 728 ($C_{39}H_{78}N_4O_4P_2$) |
| 16 | H | ethyl | melting point 134° |
| 17 | H | 2,2-dimethylpropyl | melting point 180-183° P calc. 9.61%, found 9.47% |
| 18 | $CH_3$ | n-butyl | melting point 148° |
| 19 | $CH_3$ | isobutyl | melting point 131° |
| 20 | $CH_3$ | n-octyl | viscous resin, analysis: P calc. 8.18%, found 7.9% |
| 21 | $CH_3$ | 2-ethylhexyl | oil, analysis: P calc. 8.18%, found 8.44% |

EXAMPLE 3

If 1,3-bis(2-chloro-5-ethyl-1,3,2-dioxaphosphorinan-5-yl)-2-oxapropane is reacted with 4-butylamino-2,2,6,6-tetramethylpiperidine in a procedure analogous to Example 2, 1,3-bis[2-(N-butyl-N-(2,2,6,6-tetramethyl-4-piperidyl)amino)-5-ethyl-1,3,2-dioxaphosphorinan-5-yl]-2-oxapropane is obtained as a viscous resin (Compound No. 22, formula below, $R^3 = H$); FD-MS: 730 (M+).

Analysis (731.21): P calc. 8.48%, found 8.86%.

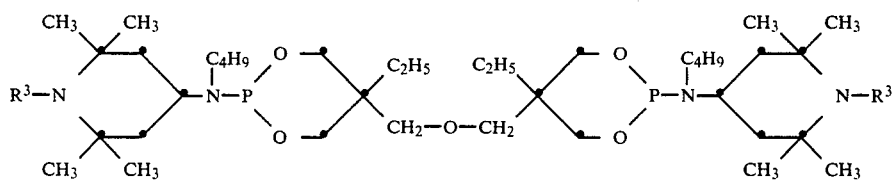

If 4-butylamino-1,2,2,6,6-pentamethylpiperidine is used as the amine in this reaction in an analogous procedure, 1,3-bis[2-(N-butyl(1,2,2,6,6-pentamethyl-4-piperidyl)amino)-5-ethyl-1,3,2-dioxaphosphorinan-5-yl]-2-oxapropane is obtained as a resin (Compound No. 23, formula above, $R^3 = CH_3$).

Analysis (759.02): P calc. 8.16%, found 8.15%.

EXAMPLE 4

15 g of N-dodecyl(1,2,2,6,6-pentamethyl-4-piperidyl)amine and 9.1 g of 2-diethylamino-5,5-dimethyl-1,3,2-dioxaphosphorinane, together with a catalytic quantity of lithium hydride, are heated in vacuo (2400 Pa) for 3 hours at 100°. The reaction mixture is distilled under a high vacuum. This gives 2-[N-dodecyl(1,2,2,6,6-pentamethyl-4-piperidyl)amino]-5,5-dimethyl-1,3,2-dioxaphosphorinane as a fraction which boils at 185°/0.1 Pa (Compound No. 24).

Analysis (470.72): P calc. 6.58%, found 6.50%.

EXAMPLE 5

100 parts of high-density polyethylene powder with a melt index of 1.7-2.3 (at 190°/21.6 kg) are mixed with 0.05 part of pentaerythritol tetrakis[3-(3,5-ditert.-butyl-4-hydroxyphenyl)propionate] and 0.1 part of the compounds according to the invention which are given in the table below, and the mixture is kneaded in a Brabender plastograph at 220° C. and 50 rpm. The kneading resistance is recorded continuously as a torsional moment during this time. In the course of the kneading period, the polymer begins to crosslink after remaining unchanged for a relatively long time, it being possible for the crosslinking to be detected by the rapid increase in the torsional moment. The time taken for the torsional moment to increase noticeably is given in the table as a measure of the stabilizing action.

TABLE 2

| Compound No. | Time in minutes |
|---|---|
| 1 | 11 |
| 3 | 15 |
| 4 | 15 |
| 5 | 12 |
| 6 | 19 |
| 10 | 10 |
| 24 | 12 |
| none | 5 |

EXAMPLE 6

100 parts of polypropylene powder with a melt index of 2.3 (at 230°/2.16 kg) are mixed with 0.1 part of calcium stearate, 0.05 part of pentaerythritol tetrakis[3-(3,5-ditert.-butyl-4-hydroxyphenyl)propionate] and 0.025 or 0.05 part of the stabilizer given in Table 3.

These mixtures are extruded on the one hand 5× in succession from a single-screw extruder at a maximum of 260° C., and on the other hand 3× in succession from the same extruder at 280° C., in each case at 100 rpm. The melt index of the polymer is measured in every case after the 1st, 3rd and 5th extrusions or after the 1st and 3rd extrusions, the load being 2160 g, the temperature 230° C. and the units of measurement g/10 min. The degradation of the polymer manifests itself as an increase in the melt index.

TABLE 3

| Stablizer | Melt index after several extrusions | | | | |
|---|---|---|---|---|---|
| | at 260° C. | | | at 280° C. | |
| | 1st | 3rd | 5th | 1st | 3rd |
| none | 6.3 | 8.9 | 15.0 | 7.1 | 21.4 |
| 250 ppm compound no. 3 | 3.6 | 6.3 | 10.8 | | |

TABLE 3-continued

| Stablizer | Melt index after several extrusions | | | | |
|---|---|---|---|---|---|
| | at 260° C. | | | at 280° C. | |
| | 1st | 3rd | 5th | 1st | 3rd |
| 550 ppm compound no. 3 | 3.2 | 3.7 | 6.0 | | |
| 250 ppm compound no. 5 | 3.9 | 6.3 | 9.0 | 4.5 | 7.7 |
| 500 ppm compound no. 5 | 3.6 | 4.9 | 7.0 | | |
| 250 ppm compound no. 6 | 3.8 | 5.7 | 8.9 | 5.3 | 14.6 |
| 500 ppm compound no. 6 | 3.4 | 4.3 | 5.8 | 5.1 | 13.9 |

EXAMPLE 7

100 parts of polypropylene powder with a melt index of 2.3 (at 230°/2.16 kg) are mixed with 0.05 part of pentaerythritol tetrakis[3-(3,5-ditert.-butyl-4-hydroxyphenyl) propionate] and 0.05 part of the compound given in the table, and the mixture is granulated in an extruder at 200°–220°. The granulated material is processed to films in an extruder with a slot die, and the films are cut into tapes. The film tapes are stretched to six times their length. The resulting tapes are 2.5 mm wide and 50 um thick. The tapes are exposed in a Xenotest 1200 until the tensile strength at break drops to half the original value. This exposure time is a measure of the light stability due to the stabilizer.

TABLE 4

| Compound No. | Exposure time |
|---|---|
| 2 | 2460 h |
| 4 | 3150 h |
| 5 | 2800 h |
| none | 630 h |

What is claimed is:

1. A compound of formula I

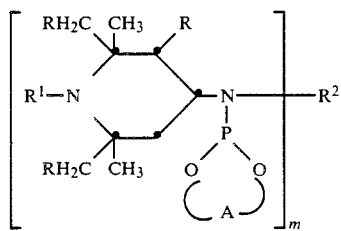

wherein
m is 1 or 2,
A is branched or unbranched 1,2-alkylene or 1,3-alkylene having 2 to 9 carbon atoms, or A is o-phenylene,
R is hydrogen or methyl,
$R^1$ is hydrogen, $C_1$–$C_{12}$-alkyl, $C_3$–$C_5$-alkenyl, $C_7$–$C_9$-aralkyl, $C_2$–$C_{12}$-alkanoyl, $C_3$–$C_6$-alkenoyl, benzoyl or cyanomethyl, and
when m is 1, $R^2$ is $C_1$–$C_{20}$-alkyl, $C_3$–$C_{14}$-alkoxyalkyl, $C_4$–$C_{12}$-dialkylaminoalkyl, $C_5$–$C_{12}$-cycloalkyl, $C_7$–$C_9$-aralkyl, $C_6$–$C_{10}$-aryl, $C_7$–$C_{20}$-alkaryl or a group of the formula IV

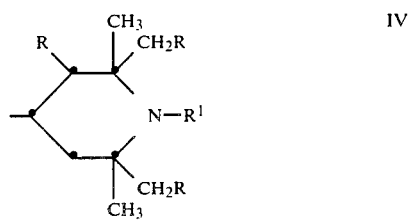

or, when m is 2, $R^2$ is $C_2$–$C_{20}$-alkylene, $C_4$–$C_{12}$-alkylene interrupted by one or more —O—, —N($C_1$–$C_4$-alkyl)— or

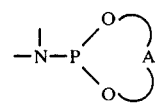

groups, or $R^2$ is cyclohexylene, xylylene, phenylene or a group phenylene-Z-phenylene or cyclohexylene-2-cyclohexylene where Z is —O—, —CH$_2$— or —SO$_2$—.

2. A compound according to claim 1 wherein
A is branched 1,2-alkylene or 1,3-alkylene,
R is hydrogen,
$R^1$ is hydrogen, methyl, allyl, benzyl or acetyl, and
when m is 1, $R^2$ is $C_1$–$C_{18}$-alkyl or a group of formula IV, or
when m is 2, $R^2$ is $C_2$–$C_{10}$-alkylene.

3. A compound according to claim 1 wherein
A is branched 1,3-propylene,
R is hydrogen,
$R^1$ is hydrogen or methyl, and
when m is 1, $R^2$ is $C_1$–$C_{12}$-alkyl or a group of formula IV, or
when m is 2, $R^2$ is $C_2$–$C_8$-alkylene.

4. A compound according to claim 3 wherein A is —CH($R^6$)—C(CH$_3$)$_2$—CH$_2$— where $R^6$ is hydrogen or alkyl of 1 to 4 carbon atoms.

5. The compound as claimed in claim 9 of the formula

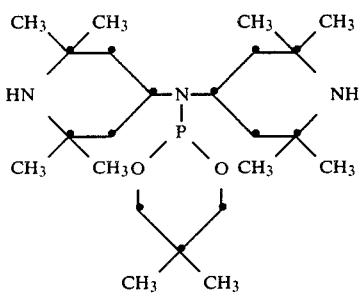

* * * * *